United States Patent
Carlson

(10) Patent No.: US 6,824,523 B2
(45) Date of Patent: Nov. 30, 2004

(54) ADJUSTABLE MOUNTING HOUSING FOR ORTHOTIC ANKLE FLEXURE JOINT

(75) Inventor: J. Martin Carlson, Mora, MN (US)

(73) Assignee: Tamarack Habilitation Technologies, Inc., Blaine, MN (US)

( * ) Notice: Subject to any disclaimer, the term of this patent is extended or adjusted under 35 U.S.C. 154(b) by 180 days.

(21) Appl. No.: 10/184,754

(22) Filed: Jun. 28, 2002

(65) Prior Publication Data

US 2004/0002672 A1 Jan. 1, 2004

(51) Int. Cl.$^7$ .................................................. A61F 5/00
(52) U.S. Cl. ............................. 602/16; 602/27; 602/28; 602/23
(58) Field of Search .............................. 602/16, 27, 28, 602/29, 23, 60, 65; 16/221, 225, 235, 238–240; 623/21.18, 47, 49

(56) References Cited

U.S. PATENT DOCUMENTS

| | | | |
|---|---|---|---|
| D316,150 S | 4/1991 | Day et al. ..................... D24/64 |
| 5,117,814 A | 6/1992 | Luttrell et al. ............ 128/25 R |
| 5,496,263 A | 3/1996 | Fuller, II et al. .............. 602/27 |
| 5,571,078 A | 11/1996 | Malewicz ..................... 602/27 |
| 5,609,570 A | 3/1997 | Lamont ........................ 602/65 |
| D385,358 S | 10/1997 | Carlson ..................... D24/192 |
| 5,716,336 A | 2/1998 | Hines et al. .................. 602/27 |
| 5,826,304 A | 10/1998 | Carlson ........................ 16/225 |
| 5,908,398 A | 6/1999 | DeToro ......................... 602/16 |
| 6,302,858 B1 | 10/2001 | DeToro et al. ................. 602/5 |
| 6,402,790 B1 | 6/2002 | Celebi .......................... 623/38 |

OTHER PUBLICATIONS

PEL Catalog, pp. 723–724, Published prior to Jun. 28, 2001.

*Primary Examiner*—Henry Bennett
*Assistant Examiner*—Amanda Flynn
(74) *Attorney, Agent, or Firm*—Westman, Champlin & Kelly, P.A.

(57) ABSTRACT

An assembly for an orthosis includes a flexure unit for joining two parts of the orthosis, such as a foot shell and an ankle or leg shell. One end portion of the flexure unit is supported on a housing that permits angular adjustment of the end portion of the flexure unit relative to the section of the orthosis on which the end portion is mounted. The angular adjustment is accomplished by utilizing a positive drive between a base portion and a housing that traps the end portion of the flexure in position on the base. This permits varying the assisting force, for example, toe lift, of the flexure unit between orthosis shell parts when the orthosis is worn.

14 Claims, 7 Drawing Sheets

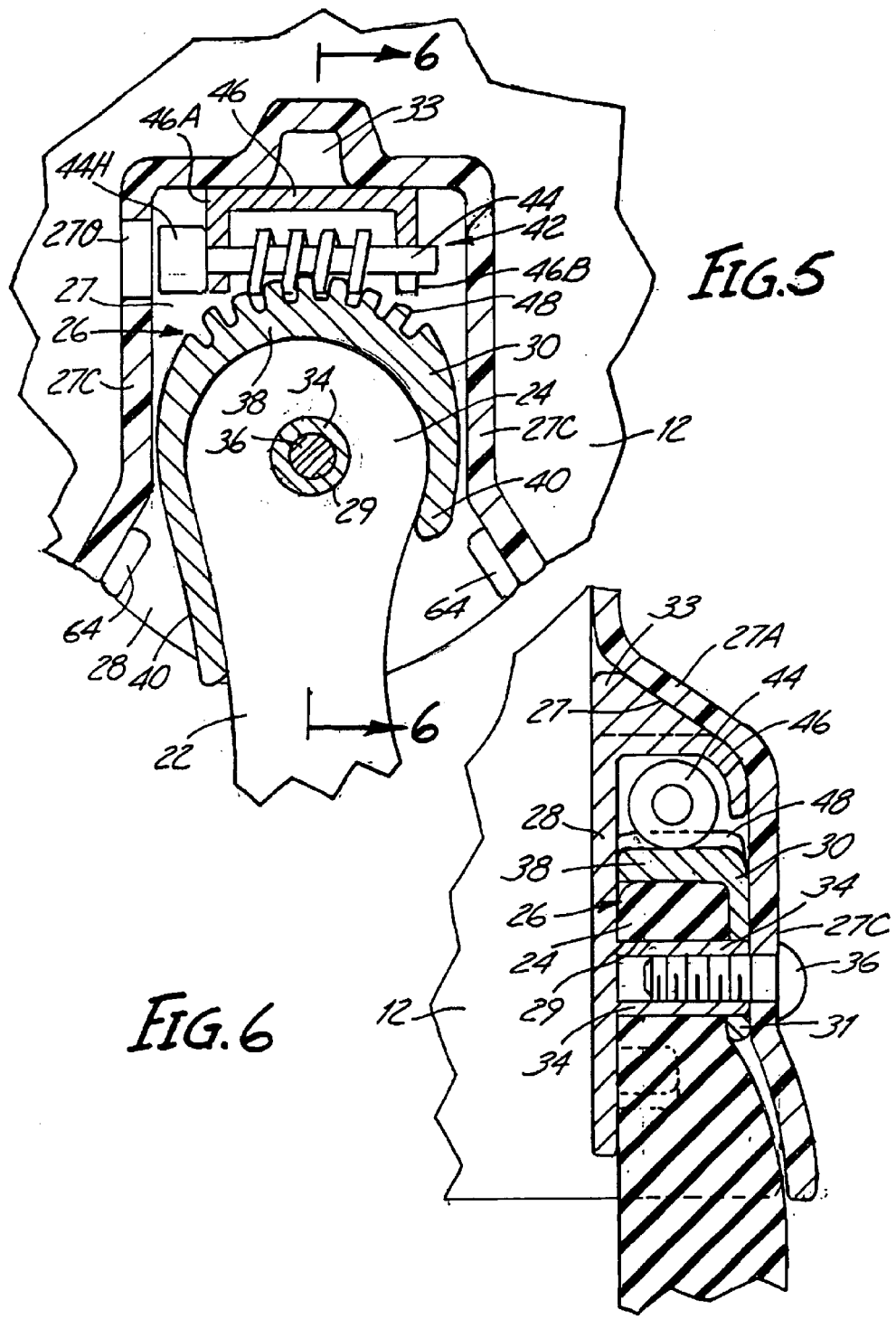

ADJUSTABLE MOUNTING HOUSING FOR ORTHOTIC ANKLE FLEXURE JOINT

BACKGROUND OF THE INVENTION

The present invention relates to mountings for flexure units that are used as hinges, specifically on orthosis to provide adjustability of the angular position of the ends of the flexure units about mounting pins used for the ends. This adjustment provides a variable assist for toe lift on an ankle joint orthosis or for the motions of other joints if so used.

Flexure units are used to provide joint motion, such as at an ankle joint, between a leg supported shell and a foot shell or stirrup. Flexure units or flexures are short columns or straps of polyurethane or other suitable thermoplastic materials. The column or strap lengths have sufficient thickness to provide a resilient bendable coupling connected between two components, for example, two parts of an orthosis shell. The flexure units function like a spring loaded hinge, and can be mounted in pairs on opposite sides of the ankle joint, for example. When used in pairs the flexure units form a joint system with a single axis of rotation passing through the flexure column midsections, that is, the elastomeric or polyurethane center portions of the flexure length. Flexures are secured, generally on pins, into shaped end cavities within the two hinged parts, such as components of a typical orthosis, including a lower leg shell and the foot support component which is called a foot shell. The elastomeric column will provide a biasing force to urge the toe of the person wearing the orthosis upwardly. The amount of toe lift force needed may be different for wearers, and can change over time for a variety of reasons.

It has been found in the prior art that flexure units can be provided with a preset angular configuration that when secured to the mounting components on the orthosis shell, the parts that are hinged together will be at an angle and when worn will provide a bias force. In the case of an ankle joint the toe lift force can be increased by angling the central longitudinal axis of the flexure unit.

In many cases it is desirable to have an adjustable amount of resilient force tending to lift the toe of a foot supported in a foot shell for meeting individual patient's needs.

SUMMARY OF THE INVENTION

The present invention relates to end supports for flexure hinge units, which are generally mounted in pairs to form a resilient pivoting joint. Flexure units that are secured between two parts of an orthosis shell including a leg shell and a foot shell, form an ankle joint hinge. At least one end of each flexure unit is mounted on the two parts, respectively, through adjustable housings that permit a change in the "at rest" angular position of the flexure unit mounted end relative to a support on the shell. The adjustment of the angular position of the one flexure end results in the ability to adjust assisting or lifting force on a foot shell, when the orthosis is worn. For example, in an orthosis shell for a foot, the amount the outer end of the foot shell portion is angled upwardly relative to the lower leg shell can be adjusted. When the orthosis is installed, and the foot shell is moved to conform to the ankle position of the wearer, the flexure units will yield to permit conforming, but a biasing force tending to return the foot shell to its at rest position will be provided. The person wearing the shell will have a force providing toe lift. Such lift force can be adjusted with the present invention.

The present invention mounting housings for the flexures include, as shown, a base that mounts onto one orthosis shell part. The base is held from rotating so it stays in position. The base has a support post that receives the end of the flexure unit or column, and a housing fits over the end of the flexure unit. The housing has an opening that fits over and pivots on the post and thus pivots relative to the base and the pivotal position is adjustable. As shown, a pinion and pinion gear drive is provided between the base and the housing at one end of the flexure. The other end of the flexure can be mounted in a conventional rivet or pin support on the other shell part, or if desired it also can be mounted with an angle adjustment housing.

The flexure unit or column used is unrestrained in its center portions between the orthosis shell parts.

The flexure end mounting housing of the present invention thus provides an adjustable angular position of the mounting housing and the end of the flexure unit held therein, about the central axis of the post that mounts the flexure unit.

In the specific form shown, the base mounts a pinion or screw, which engages rack or pinion teeth on the outer end surface of the mounting housing. By turning the pinion, a rack and pinion drive is provided to pivot the mounting housing relative to the base to its desired angular position. The change in angle varies or changes the assisting force for toe lift. The pinion and gear effect can be calibrated so the change in assisting force for each turn of the pinion may be determined.

If desired, both of the mountings for the flexure unit may have this adjustable end supports that can be changed in angular orientation about the mounting axis of the flexure unit relative to its support.

The unrestrained central portion of the flexure forms a hinge, and resiliently conforms to pivoting action to provide an ankle joint or other suitable joint where a controlled pivotal mounting is desired.

In the case of an ankle-foot orthosis, the dorsiflexion/planterflexion of the patient's ankle can be differently loaded by adjusting the angular position of the mounting housings for the flexure ends relative to their base supports.

Other types of angular adjustment drives between the mounting housings and the base or mounting components can be used. For example various threaded components that would act against portions of the flexure mounting housing to provide a positive change in angular position and hold the mounting housing in such changed angular position can be used.

BRIEF DESCRIPTION OF THE DRAWINGS

FIG. 5 is a fragmentation side elevational view of a flexure unit mounting housing and base according to a preferred embodiment of the present invention with the shell covering broken away;

FIG. 6 is a sectional view taken on line 6—6 in FIG. 5;

DETAILED DESCRIPTION OF THE PREFERRED EMBODIMENTS

Figure 1:
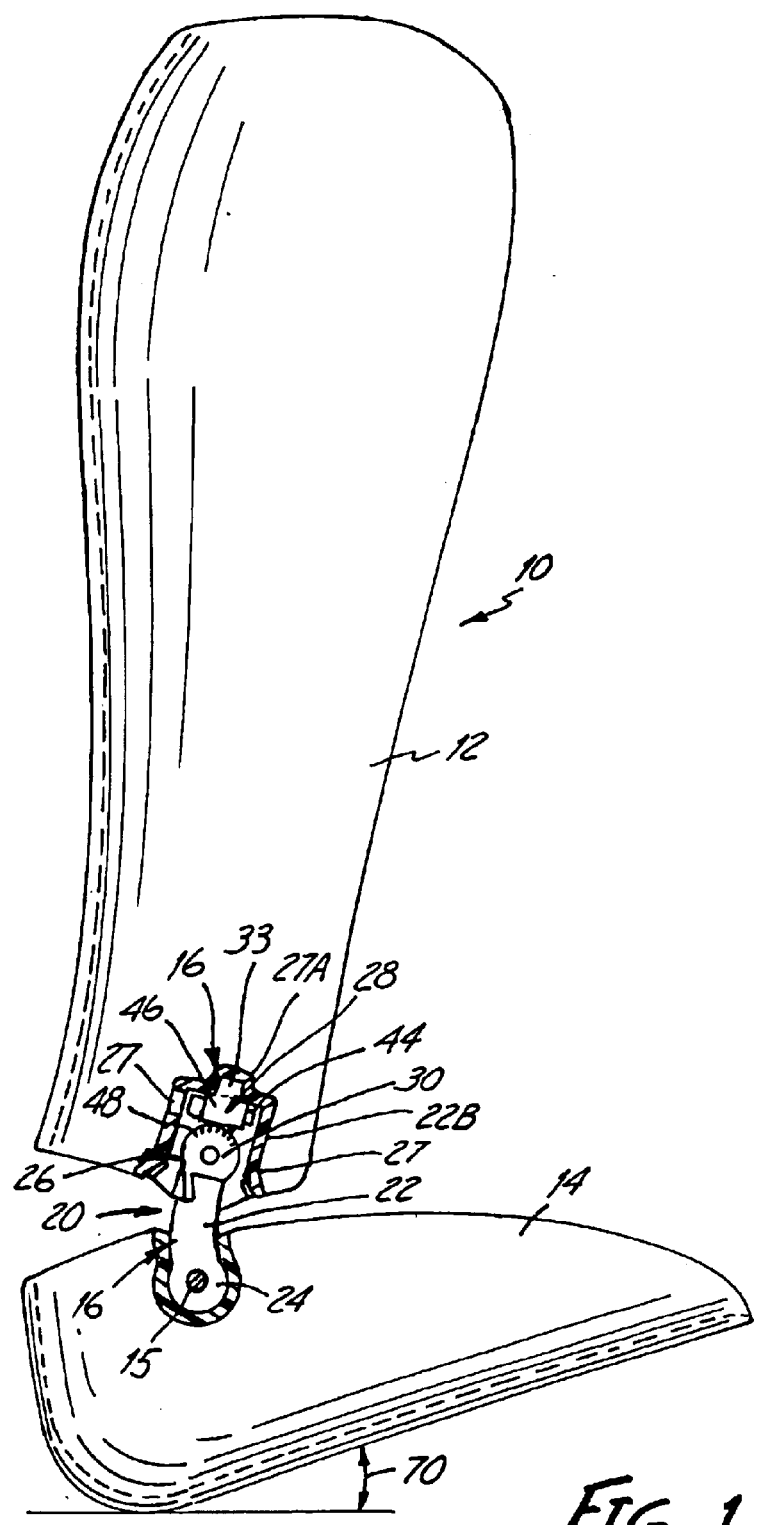
FIG. 1 is a side elevational view of an orthosis shell having an orthosis foot support shell and lower leg shell held together with a flexure unit hinge mounted in accordance with the present invention.
Figure 2:
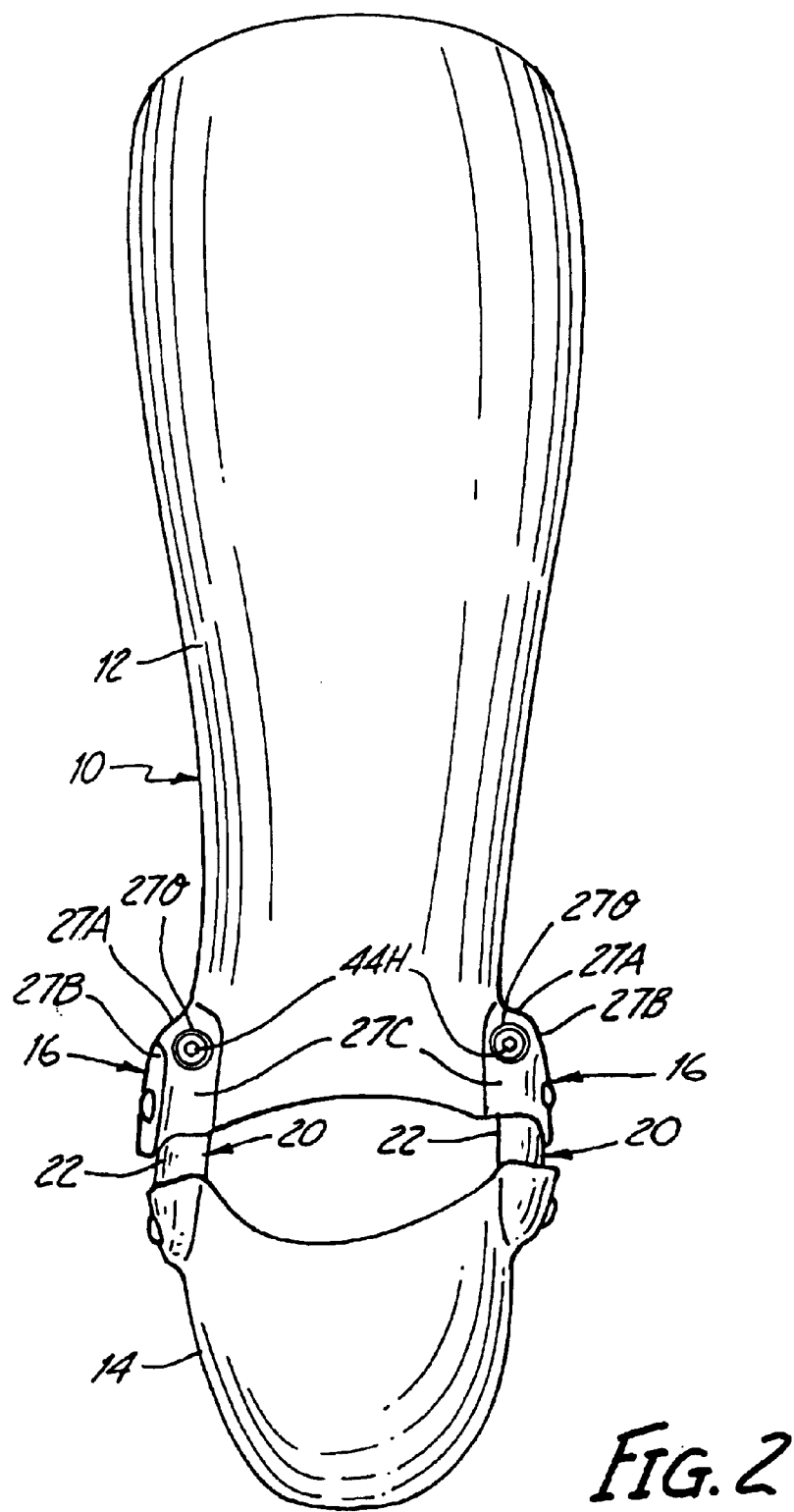
FIG. 2 is a rear view of the orthosis shell of FIG. 1.
Figure 3:
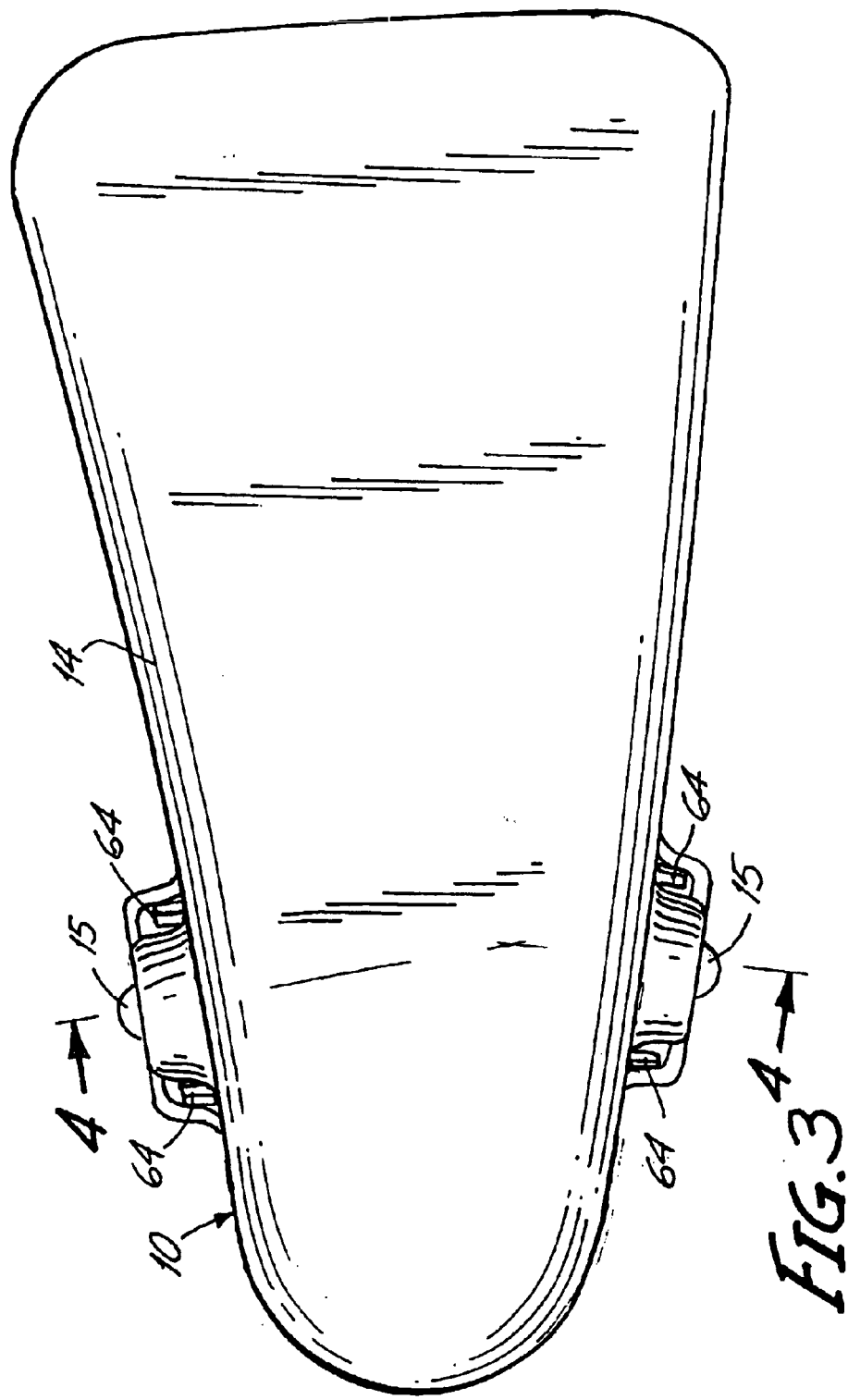
FIG. 3 is a bottom view of the orthosis shell of FIG. 1.

An orthosis assembly 10 is used in connection with an ankle joint, and the assembly includes a leg support shell 12 that fits around rear portions of a lower leg of a wearer, and it can be strapped in place in a normal manner. A foot shell 14 is used for supporting the foot of a wearer and moves about an ankle joint of the wearer. Shell sections 12 and 14 are joined together with a flexure assembly 16 on each side of the shells, forming an ankle joint. The flexure assembly 16 has right and left forms, and the right hand assembly is shown in detail. The left side is a mirror image of the right side.

The flexure assembly 16 made to provide a biasing force for positioning the foot shell 14 relative to the lower leg shell section 12, and to provide a certain amount of bias in an upward direction so that there is a "toe lift" action or assist by the flexure assembly 16. The flexure assembly, as can be seen, includes a flexure unit or column 20 which is made of a suitable elastomeric material, such as polyurethane material. The flexure unit can be made in the manner shown in U.S. Pat. No. 5,826,304. The flexure unit or column 20 has a center elastomeric column portion 22 that is in turn extends between end or fastening portions 24 (see FIG. 5). The lower end of the flexure unit or column 20 as shown is connected to the foot shell 14 with a non-adjustable connection 15 such as a rivet or screw, as is done in prior art.

The upper end portion 24 is mounted as shown, in an angularly adjustable flexure unit mounting assembly 26, that permits pivoting the end portions 24 about a central axis of a bore 29 in each end portion 24 that is used for mounting the flexures. The bores 29 may have bushings in the bores for strength. The bores 29 fit on posts 34 on bases or plates 28.

Each of the adjustable mounting assemblies 26 includes a base or base plate 28 that is on the interior of an inwardly opening recess 27 formed by walls 27A, B and C that protrude on the sides of shell section 12. The base plates are held securely on shell section 12.

The base plates 28 have upper end lugs 33 that fit into a slot in the top wall 27A forming part of recess 27 to prevent rotation of the base plate 28 relative to the shell post 12. Other types of fasteners can be used to insure the base plate 28 will not move relative to the shell.

Figure 4:
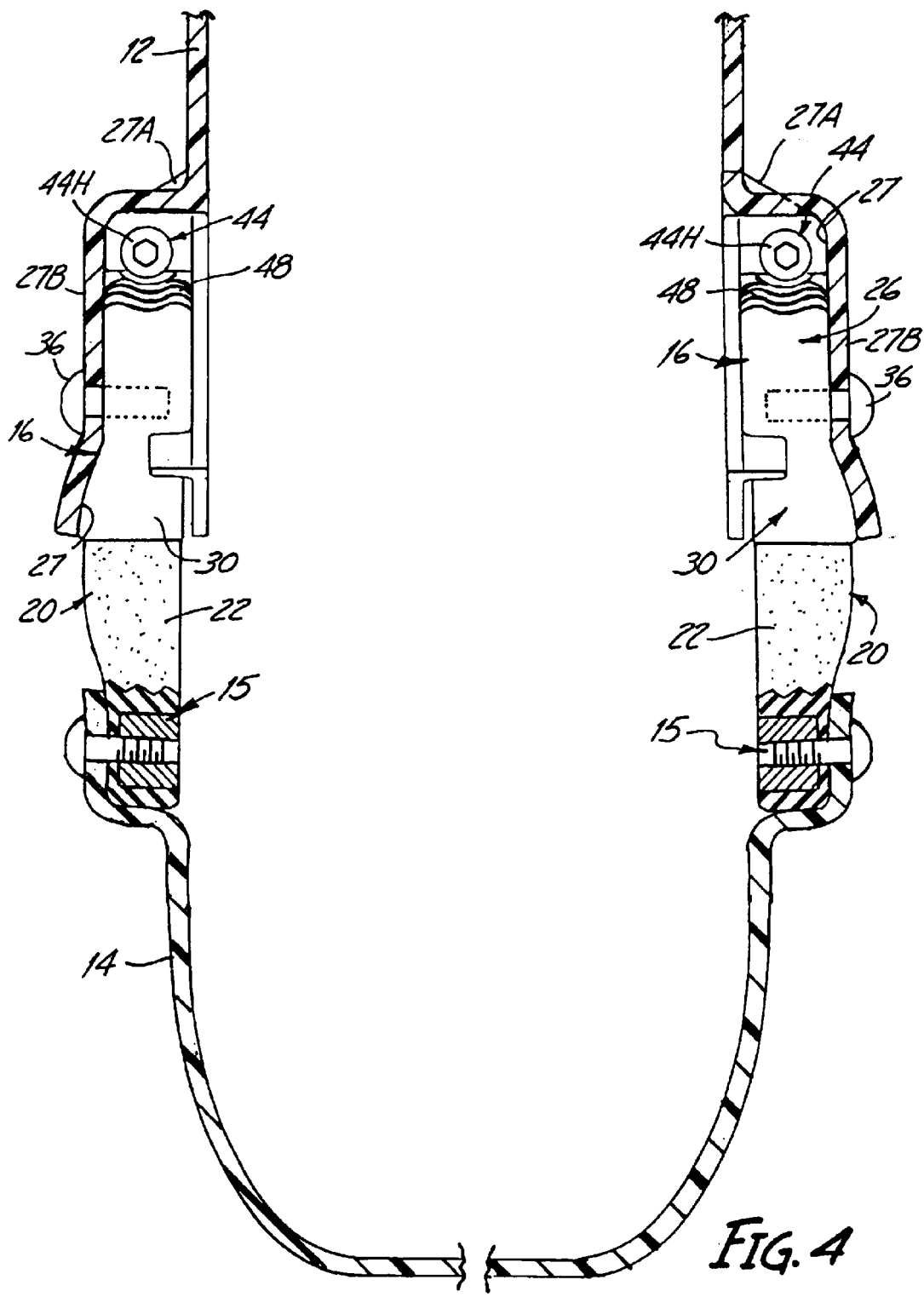
FIG. 4 is a sectional view taken as in line 4—4 in FIG. 3.

The end portion 24 of each flexure unit or column 20 is retained on a post 34 on the base plate 28 within an overlying adjustable housing 30. The housing 30 captures and supports the respective end portion 24 of a flexure unit. The housing 30 has a wall 31 (FIGS. 6 and 7) at a side thereof which is parallel to the base plate 28, and adjacent wall 27B forming a recess 27 on shell post 12. (See FIG. 4) A bore 50 fits over the post 34 mounted on the respective base plate for pivotally mounting the housing 30. A threaded screw 36 is threaded into a bore in the post 34 and has a head that bears on wall 27B for retaining the housing 30 in position on the respective post 34. The post 34 is integral with the base or base plate 28 and the base plate is secured to wall 27B forming part of recess 27 with the screw 36 as well. The head of the screw clamps the wall 27B against the end of post 34. The housing 30 traps the associated end portion 24 of the flexure unit 20 for pivotal movement about the post 34. The screw 36 and lug 33 serve to mount the base 28 securely.

An integral edge wall 38 curves around the end of the housing 30 as seen in FIG. 5, and wall 38 joins reaction walls 40 at the first and rear sides of the housing 30 that restrict movement of the flexure end 24 relative to the housing. Walls 38 and 40 are perpendicular to wall 31 and the end portion 24 is confined so the end of the flexure moves with the housing. The respective end portion 24 of the flexure unit held in the respective housing 30 will pivot on post 34 only by pivoting the housing 30. The pivoting of the housing 30 about its mounting post 34 is controlled with manual adjustment drive device 42 that in the form shown, comprises a rotatable threaded drive comprising a pinion or screw 44 supported in a pinion retainer frame 46 on the upper portion of the base plate 28. The pinion is positioned to engage reaction members comprising rack teeth or pinion gear teeth 48 on the upper periphery of wall 38 of housing 30, when housing 30 is in place on pin 34.

As shown in FIGS. 5 and 6, the pinion 44 has screw threads that engage the teeth 48, and when the pinion 44 is rotated, the housing 30 will be caused to pivot about the axis of post 34, and change the angular orientation of the end portion 24 of the flexure unit 20 held by that housing. The thread lead angle of the pinion 44 is such that the housing 30 is held in position, because loads the housing 30 cannot drive the pinion 44 in reverse. The pinion 44 has a drive head 44H accessible through an opening 27D in a rear wall 27C of the recess 27.

Again, the housing 30 has side or edge walls 40 that engage and trap edges of the end portions 24 of the flexure unit 20 in position. The end portion 24 of the flexure unit 20 is changed in mounting angle when the housing 30 is adjusted with the pinion and pinion gear.

Figure 7:
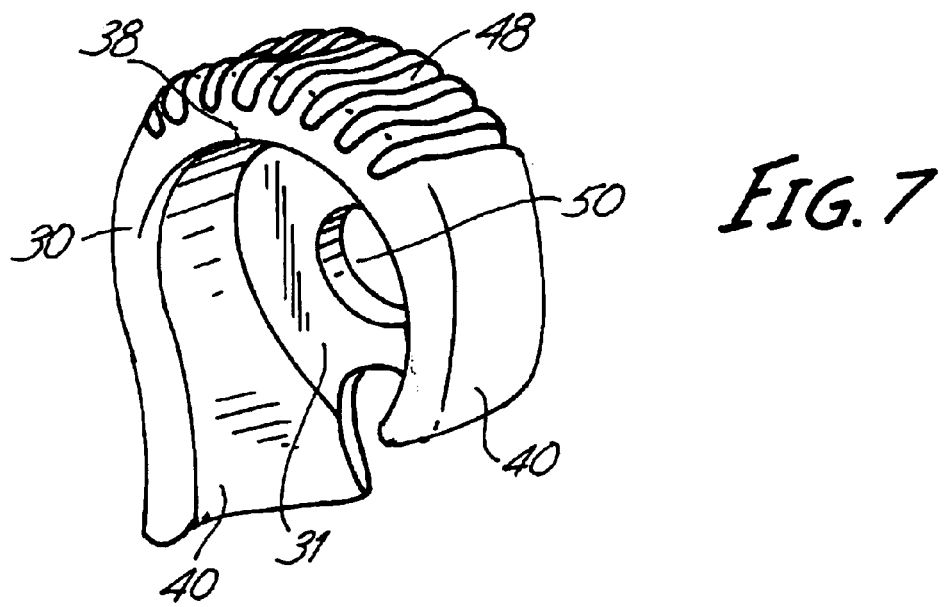
FIG. 7 is a perspective view showing an interior of the outer mounting housing of the present invention.

In FIG. 7, the gear teeth 48 are shown as well as the interior of the housing 30.

Figure 8:
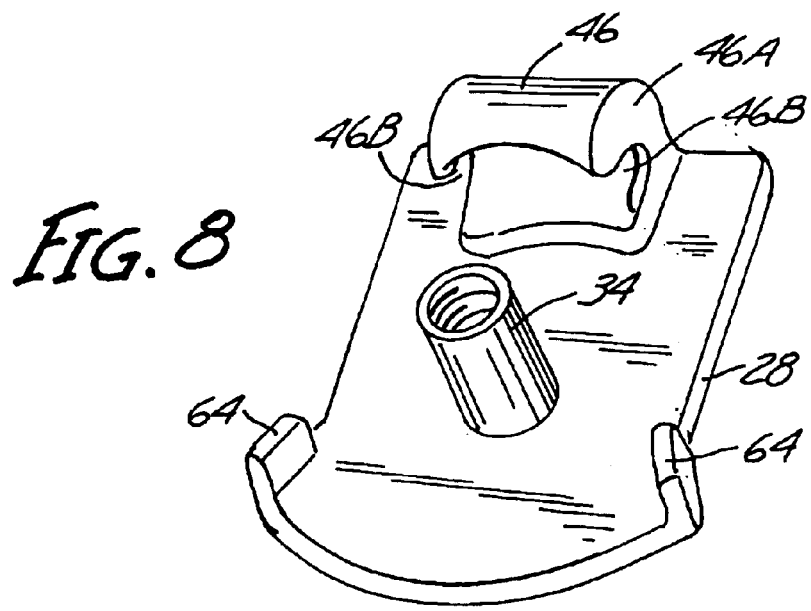
FIG. 8 is a perspective view of a typical base portion showing a mounting post for a flexure unit.

In FIG. 8, a perspective view of a base plate 28 is shown, in its preferred form. As can be seen, the post 34 protrudes from the base plate 28 at right angles. It can be seen that the pinion housing 46 has end walls 46A with recesses 46B that will receive the center rotatable shaft portion of the pinion 44. The threads of the pinion fit inside the housing 46. The relationship between recesses 46B and the post 34 can be maintained so that the gear teeth 48 of the housing 30 are engaged by the threads on the pinion when post 34 is in the bore 50.

In order to adjust the toe lift or assist force, the housings 30 on each side of the orthosis can be pivoted about the axis of the posts 34 on the respective base plate 28, by rotating the pinions. As shown in FIG. 1, the bottom of foot shell 14 has a lift angle 70 at rest, which is the toe lift, and that angle can be changed by moving the housings 30 on each side of the orthosis. The mounting of the base plates 28 and housings 30 is done so that the axis of pivoting of the center portions of the flexure units 20 is substantially aligned with the axis of movement of the ankle of a wearer. The ankle axis can actually shift slightly as the foot is moved, and by proper adjustment the center portions 22 of the flexures 20 can be aligned appropriately.

Figure 9:
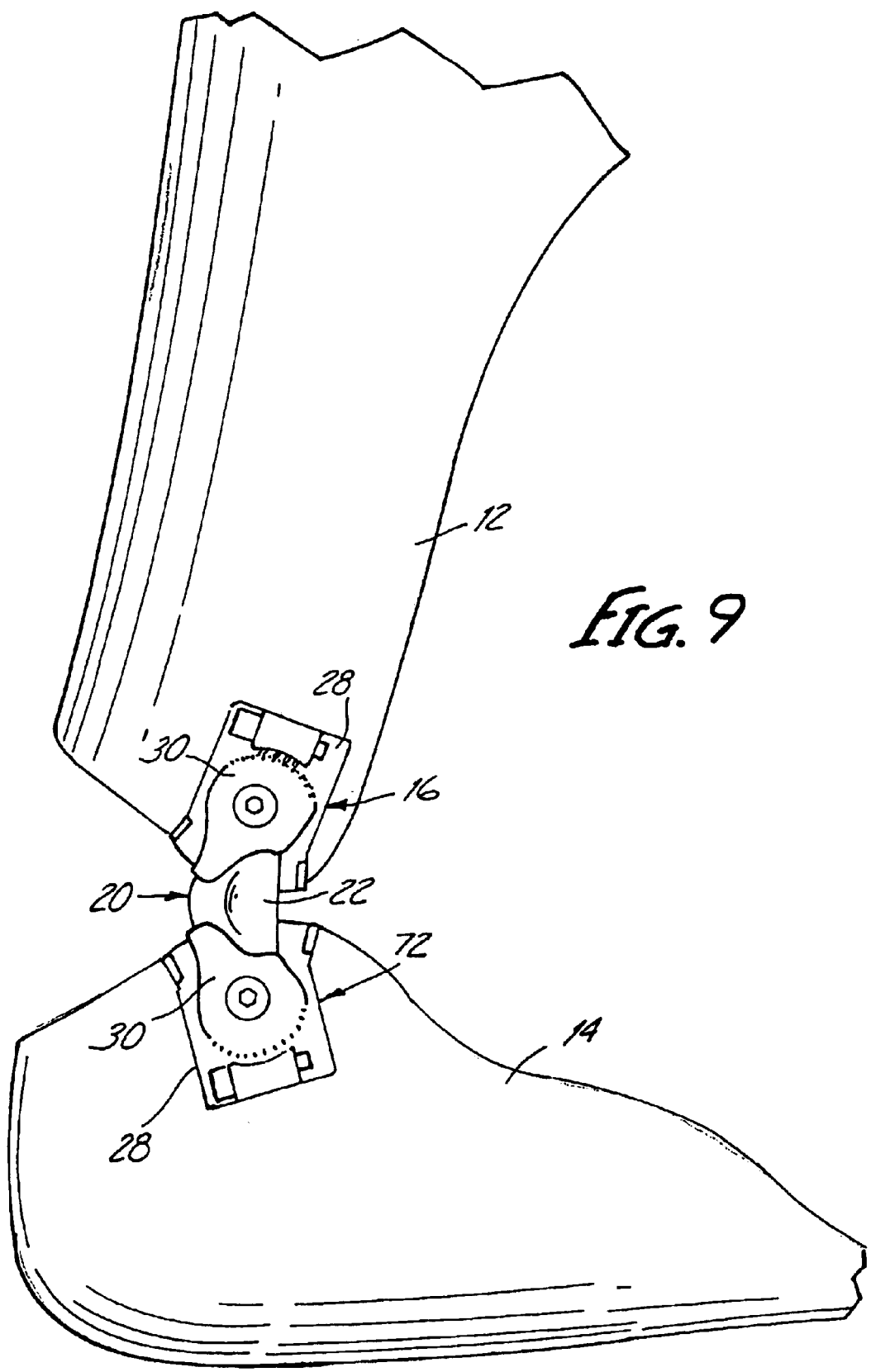
FIG. 9 is a schematic side view of an alternate embodiment with angle adjustments at both ends of the flexure.

The adjustable mounting housing 30 is preferably on only one of the ends of the flexure units 20, as shown, but if desired, both ends of each flexure can be adjustably mounted for obtaining adjustable toe lift as shown schematically in FIG. 9 where a lower angle adjustment device 72 is illustrated. The lower adjustment device operates as described. The inner surfaces of the base plates can be suitably padded to provide comfort.

The base plates 28, as shown in FIG. 8, also have stop walls 64 along the edges at the ends of the base plate opposite from the pinion housing 46, to limit the amount of pivotal movement of the mounting housings 30 so that they do not move excessively.

The edges of the walls 40 of the mounting housing 30 can be flared and radiused to avoid unnecessary wear on the flexure units. The amount of toe lift can be easily adjusted to accommodate individual users.

Again, mounting housings 30 are used on the opposite sides of one or both of the flexure shells, and certain parts will have to be right and left hand orientation, or in other words mirror images of each other. The base plates 28 and housings 30 can be molded, cast metal, or machined as desired.

The material used for the flexure units 20 is not critical, as long as the material is elastomeric, and flexible, to permit adequate hinging movement for the orthosis.

The adjustment devices can be on the exterior of the shells, if desired.

Although the present invention has been described with reference to preferred embodiments, workers skilled in the art will recognize that changes may be made in form and detail without departing from the spirit and scope of the invention.

What is claimed is:

1. A mounting assembly for a flexure unit wherein the flexure unit comprises a unitary resilient column extending between and permitting hinging movement between first and second orthosis parts by bending the column from a rest position of the parts, the mounting assembly including a base attachable to one of the parts, a support on the base for supporting one end of the flexure unit, a mounting housing trapping an end portion of the flexure unit and retaining the end portion on the support, and an angular adjustment device for angularly adjusting the position of the mounting housing relative to the base about an axis perpendicular to the base to cause a change in the rest position of the parts relative to each other.

2. The mounting assembly of claim 1 wherein the adjustment device comprises a rotatable pinion on one of the base and the mounting housing, and a pinion gear engaged by the pinion and mounted on the other of the base and mounting housing, whereby rotation of the pinion causes movement of the pinion gear to control relative pivoting of the mounting housing and base about the axis.

3. A mounting assembly for a flexure unit for permitting hinging movement between first and second orthosis parts, including a base attachable to one of the parts, a support on the base for supporting a flexure unit, a mounting housing having walls to trap and support an end portion of the flexure unit and retain the end portion on the support, and an angular adjustment device for angularly adjusting the position of the mounting housing relative to the base about an axis perpendicular to the base to control movement of the flexure unit about the axis.

4. The mounting assembly of claim 1 wherein the support comprises a post protruding substantially perpendicular to a plane of the base, said axis being a central axis, the flexure unit and mounting housing being pivotally mounted on the post, such that the adjustment of the mounting housing causes pivoting of both the flexure unit end portion and the mounting housing about the axis of the post.

5. The mounting assembly of claim 4 wherein the base comprises a base plate, and said mounting housing has a wall that is parallel to the base plate when installed on the post on the base plate, said wall covering an outer side of the end portion of the flexure unit and preventing outward movement of the flexure unit relative to the base plate.

6. The mounting assembly of claim 1 wherein the angular adjustment between the mounting housing and the base is controlled by a pinion and pinion gear drive arrangement.

7. The mounting assembly of claim 5 wherein the base plate has stop members thereon that stop pivoting of the flexure unit in both directions of pivoting from a center position with the parts in the rest position.

8. The mounting assembly of claim 2 wherein the pinion is rotatably mounted on the base.

9. The mounting assembly of claim 1 wherein the mounting housing has a side wall and an edge wall at right angles to the side wall, the edge wall overlying edges of the end portion of the flexure unit, and the side wall being spaced from the base, the end portion of the flexure unit being between the side wall and the base.

10. In combination with an orthosis having a pair of support shells including a foot shell and a leg shell, and flexure units have aligning resilient flexible portions on opposite sides of the shells to form an ankle joint by bending the flexure units between the leg shell and foot shell, the improvement comprising a mounting assembly for at least one end of each of the flexure units, each mounting assembly comprising a base supported on the respective shell, a support on the base for pivotally mounting an end portion of a flexure unit on the base, a mounting housing pivotally mounted on the support on the same pivotal mounting as the respective end portion, and holding and retaining the end portion on the support, and an adjustment device between the base and the mounting housing to permit changing the angular position of the mounting housing and the end portion of the flexure unit held thereby about the pivotal mounting relative to the base.

11. The combination of claim 10, wherein the adjustment device comprises a rack and pinion drive between the base and the mounting housing.

12. A variable angle mounting for a resilient column flexure unit comprising a base adapted to be supported onto an orthosis shell, said base having a mounting post extending therefrom, said post having a central axis and being of size to receive and pivotally support an end portion of a flexure unit, a housing supported on the post and having wall portions to overlie end portions of a flexure unit on the post, and a manual drive assembly to vary the angular position of the housing relative to the base about the post, the drive assembly comprising a rotatable threaded drive on one of the base and housing, and a reaction member on the other of the base and housing, the reaction member being moved by the threaded drive when the threaded drive is rotated.

13. The variable mounting of claim 12 wherein the drive comprises a pinion and pinion gear drivably coupled between the base and the housing.

14. The variable mounting of claim 13 wherein the housing has a curved wall at one end formed on a radius about the central axis, the curved wall having pinion gear teeth thereon, and a support on the base for mounting a pinion in position to engage the gear teeth, the pinion comprising the threaded drive and the pinion gear teeth comprising a plurality of reaction members.

\* \* \* \* \*

UNITED STATES PATENT AND TRADEMARK OFFICE
CERTIFICATE OF CORRECTION

PATENT NO. : 6,824,523 B2
DATED : November 30, 2004
INVENTOR(S) : Carlson

It is certified that error appears in the above-identified patent and that said Letters Patent is hereby corrected as shown below:

Title page,
Item [56], References Cited, U.S. PATENT DOCUMENTS, add
-- 5,086,760
5,224,925
5,460,599
5,520,627
5,573,501
5,836,903
4,669,457
5,496,263
4,934,355
5,044,360
5,014,690
5,571,078 --

Signed and Sealed this

Tenth Day of May, 2005

JON W. DUDAS
*Director of the United States Patent and Trademark Office*